US005457325A

United States Patent [19]

Huberty

[11] Patent Number: 5,457,325

[45] Date of Patent: Oct. 10, 1995

[54] CONTACT-FREE PROCEDURE FOR MEASURING THE THREE DIMENSIONAL SHAPE OF AN OBJECT, PARTICULARLY A HUMAN FOOT, BY IMAGING THE OBJECT AND THE INDENTATION LEFT BY THE OBJECT

[75] Inventor: Stéphane Huberty, Allée de la Coisse, F-30110 Branoux, France

[73] Assignees: Stephane Huberty; Ideas, both of Brussels, Belgium

[21] Appl. No.: 182,049

[22] PCT Filed: Jul. 15, 1992

[86] PCT No.: PCT/FR92/00679

§ 371 Date: Apr. 21, 1994

§ 102(e) Date: Apr. 21, 1994

[87] PCT Pub. No.: WO93/18336

PCT Pub. Date: Feb. 4, 1993

[30] Foreign Application Priority Data

Jul. 15, 1991 [FR] France .................................. 91 08895

[51] Int. Cl.[6] .............................. G01N 21/86; G01V 9/04

[52] U.S. Cl. ...................... 250/559.29; 356/376; 348/139

[58] Field of Search .................................... 250/561, 558; 348/135, 139; 12/146 L; 356/376, 12, 13, 14

[56] References Cited

U.S. PATENT DOCUMENTS

| | | | |
|---|---|---|---|
| 3,457,647 | 10/1966 | Cohen | 33/3 |
| 4,634,279 | 1/1987 | Ross et al. | 356/376 |
| 4,654,872 | 3/1987 | Hisano et al. | 382/1 |
| 4,724,526 | 2/1988 | Cole et al. | 364/562 |
| 4,745,290 | 5/1988 | Frankel . | |
| 4,980,763 | 12/1990 | Lia | 358/98 |
| 4,982,438 | 1/1991 | Usami et al. | 382/25 |
| 5,027,461 | 7/1991 | Cumberland | 12/142 N |

FOREIGN PATENT DOCUMENTS

| | | |
|---|---|---|
| 0014022 | 8/1980 | European Pat. Off. . |
| 5866004 | 4/1983 | European Pat. Off. . |
| 2580487 | 10/1986 | France . |
| 3508730 | 9/1986 | Germany . |
| 9005345 | 5/1990 | WIPO . |

*Primary Examiner*—David C. Nelms
*Assistant Examiner*—Steven L. Nichols
*Attorney, Agent, or Firm*—Helfgott & Karas

[57] ABSTRACT

A contact-free tridimensional process for measuring the form of an object, such as a foot, using digitization. This process consists of setting the object on a flexible cradle, for the two-phase measurement of the object. The first phase covers the upper part of the object. Once the object has been removed from its support, the second phase consists of measuring its imprint. Both parameters measured are processed in order to reconstitute the complete outer shape of the object. The device used to perform this process requires sensors which take pictures, and a computer. This process and device are specially relevant to the production of made-to-measure footwear of both the orthopaedic and non-orthopedic variety.

14 Claims, 4 Drawing Sheets

9 5 6 4 12 14 13 7 11 3 15 1 8 2 X

CONTACT-FREE PROCEDURE FOR MEASURING THE THREE DIMENSIONAL SHAPE OF AN OBJECT, PARTICULARLY A HUMAN FOOT, BY IMAGING THE OBJECT AND THE INDENTATION LEFT BY THE OBJECT

BACKGROUND OF THE INVENTION

This invention concerns a contact free tridimensional process for measuring the outer shape of an object, specifically a human foot, with a view to making made-to-measure footwear, whether or not of the orthopaedic variety.

This measurement process can also be extended to all tridimensional objects.

This invention also concerns the measurement equipment used for the process.

The various stages of made-to-measure show production consist in measuring the foot, producing, on the basis of measurement recorded, a last currently and hereinafter designated "last", measuring this last and, on the basis of measurements recorded, cutting out the various parts designated "patterns" from some material such as leather; then finally assembling these sundry parts primarily by means of stitching and bonding, the last being used as a support.

The first phase of this invention process, therefore, applies to the production of a made-to-measure shoe, that is to say a shoes which is made to fit the foot.

One known measurement procedure consists in manually measuring the foot using a tape. This system presents a number of drawbacks. Indeed, there is contact between the tape and the foot; there will be variations in tape tension and positioning; these all introduce variables into the measurements, the number of which are limited to a few peripheral and contour records (between 5 and 10), and, finally, it is impossible to obtain accurate measurements in space using this system. Thus the tridimensional form data can be regarded as virtually nil since only projections and perimeters are measured.

Another current contact-free process consists in measuring the foot using a "cross hatching" technique or a single laser plane associated with a photographic picture, which, when connected to a computer, define three coordinates for each measurement point. This digitization measurement technique is more accurate than the manual measurement system but the foot is measured "without load", i.e. it does not bear on the ground. This "no-load" system means that the sole of the foot can be measured directly. However, it presents a major drawback since the shape of the foot will alter when it is under load (when the person is standing) and "no-load" measurements will not apply to the "loaded" foot configuration.

Therefore, this system furnishes distorted data and, further, requires a much greater number of reference points in order to measure the sole and the arch of the foot.

Summary of the Invention

This invention aims to ensure a perfect match between the foot shape and the shoe made for it, thus affording the wearer great comfort. The aim is achieved by measuring the "loaded" foot, therefore, under real shoe usage conditions and with fewer reference points, thereby reducing the cost of measurement equipment.

This invention concerns a contact-free tridimensional measurement process, of the outer shape of an object, more specifically the foot, by digitization with at least one sensor connected to a computer.

According to the invention, this process consists in positioning the object on a flexible cradle, and in the two-phase measurement of the object; the first phase covers the upper part of the object; once the object has been removed from its support, the second phase consists in measuring its imprint, both parameters measured being processed in order to reconsititute the complete outer shape of the object.

According to one of the properties of the invention, this process consists in two pictures being taken for the first measurement phase and one picture being taken for the second measurement phase. Priority should be given, in the case of the two first phase measurement pictures to either a posterior, superior and axial shot and to one anterior, superior and axial shot, or to a posterior, superior and lateral shot and one posterior, superior and medial shot.

As an option, in the two picture case, one lateral and one medial, this process requiring a third picture which will be superior, axial, anterior or posterior.

According to another of the invention's properties, this process consists in a picture being taken for the second measurement phase and this will be superior, axial, anterior or posterior.

The second measurement phase can also embody two pictures, two superior, axial shots, one being anterior and the other posterior, or one posterior, superior lateral shot and one posterior, superior and medial shot.

This invention also concerns equipment for the tridimensional measurement of the shape of an object using digitization via a sensor linked to a computer.

According to this invention, this equipment incorporates a flexible cradle to support the object to be measured.

Each sensor consists of a projector and a camera which form a specific angle to each other, the projector and the camera being positioned at a specific distance from each other.

The main projector and camera axes converge at a point near to or within the object to be measured. Preferably, the projectors will be of the multiple luminous plane type. The intersection of these luminous planes with the object to be measured trace on the latter intersections formed by the luminous plane with the object's outer surface. One or more of these planes is singled out and enables the subsequent planes to be positioned at specific intervals. The camera records these intersections and transmits them to the computer. As the angle and distance connecting the projector and each of these planes with the camera are known factors, the computer uses triangulation to establish the three dimensions of the object measured within the sensor's field of vision.

According to the first modus operandi, the equipment has a single sensor which consists of a projector and a camera; the sensor is mobile for taking shots from at least two viewing angles.

According to the second modus operandi, this equipment comprises several sensors at fixed positions in space.

According to one of the second method modus operandi, both sensors are positioned along the axis of the cradle, one taking a posterior superior shot and the other taking an anterior superior shot.

According to a second example of second method modus operandi, both sensors are out of line in relation to the axis of the cradle, one taking a posterior, superior and lateral shot, the other a posterior, superior medial shot.

BRIEF DESCRIPTION OF THE DRAWINGS

For guidance and with reference to the attached drawings, there follows the description of equipment which according to the invention is used to measure the object which is, in this case, a foot.

DETAILED DESCRIPTION OF THE PREFERRED EMBODIMENT

Figure 1:
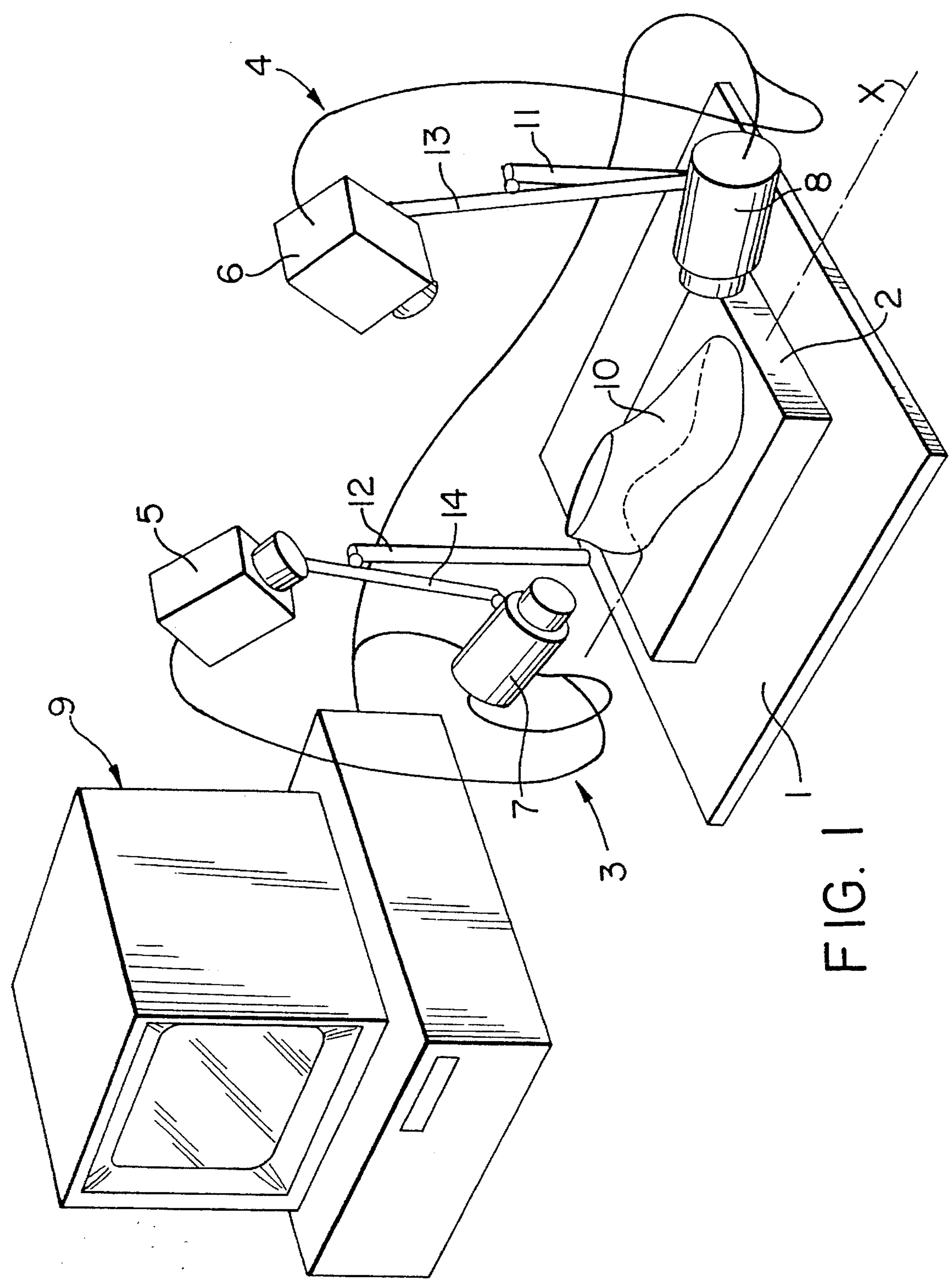
FIG. 1 shows the equipment subject of the invention equipped with two sensors located within the axis of the cradle and measuring the upper part of the foot supported in a flexible cradle; this constitutes the first measurement phase.

In FIG. 1, the equipment has a base 1, a flexible cradle 2, two sensors 3,4 which each consist of a camera respectively 5, 6 and a projector respectively 7,8 and finally a computer respectively 9, both cameras and, if applicable both projectors, being linked into the computer.

Flexible cradle 2 is supported on base 1, and a foot 10 shown as an approximation, rests on cradle 2 of a remanent construction such as micro-pellets or foam.

The ends of base 1 are fitted with two posts 11, 12; post 11 takes the arm 13; the ends of this arm support sensor 3's camera 5 and projector 7, and post 12 has an arm 14 the ends of which support sensor 4's camera 6 and projector 8.

Both sensors 3,4 are positioned along the main X axis of the base 1; ideally the axis of the foot should be located along this axis.

The heel of the foot points at sensor 3 in such a way that camera 5 takes a posterior, superior and axial shot and camera 6 takes an anterior, superior and axial shot.

Figure 2:
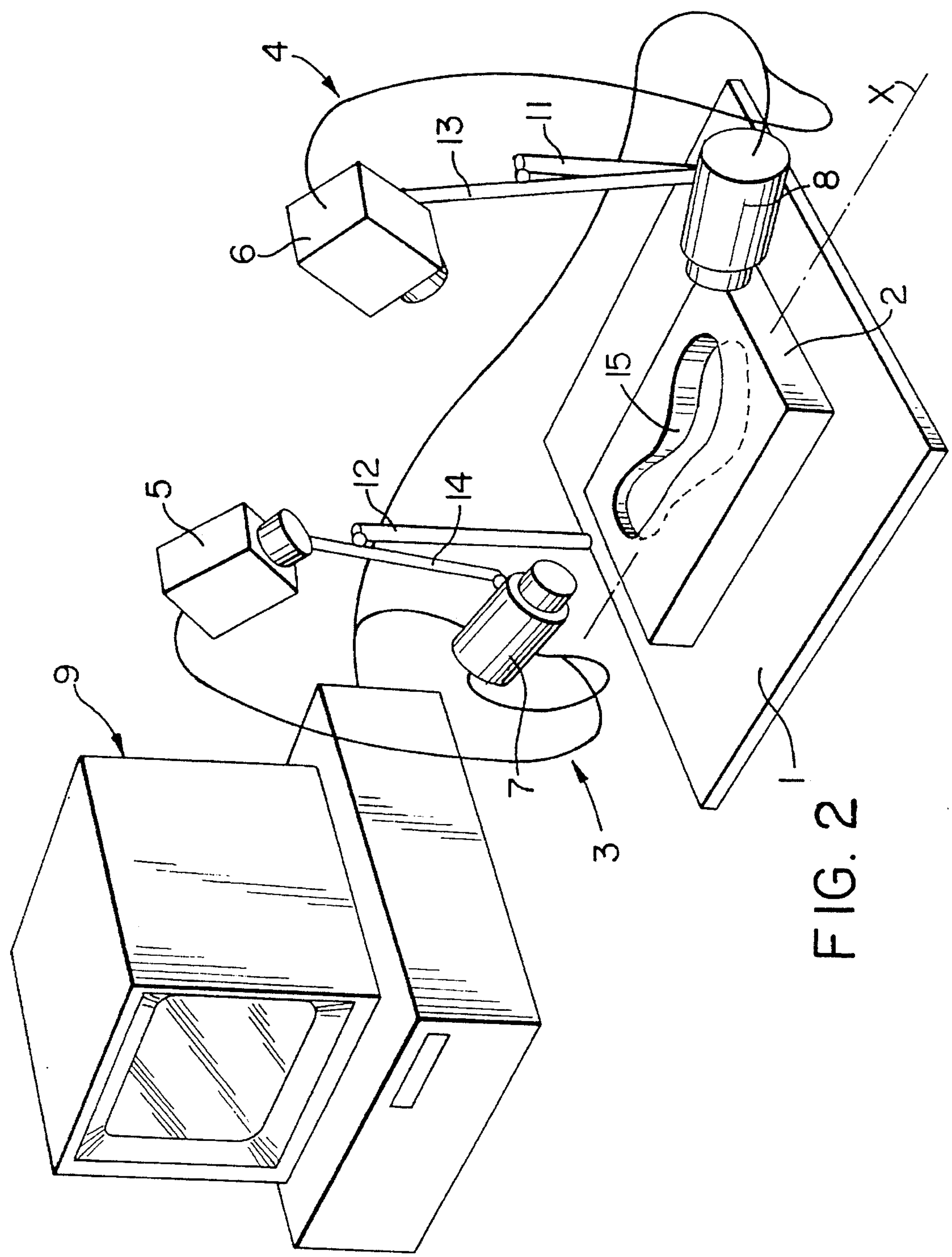
FIG. 2 shows the equipment covered by the invention with the same sensors measuring the imprint of the foot on the flexible cradle; this constitutes the second measurement phase.

FIG. 2 is identical to FIG. 1 with regard to the sensor position. The foot has been removed from the flexible cradle, leaving only an imprint 15. Both cameras 5,6 each take a measurement of this imprint.

Figure 3:
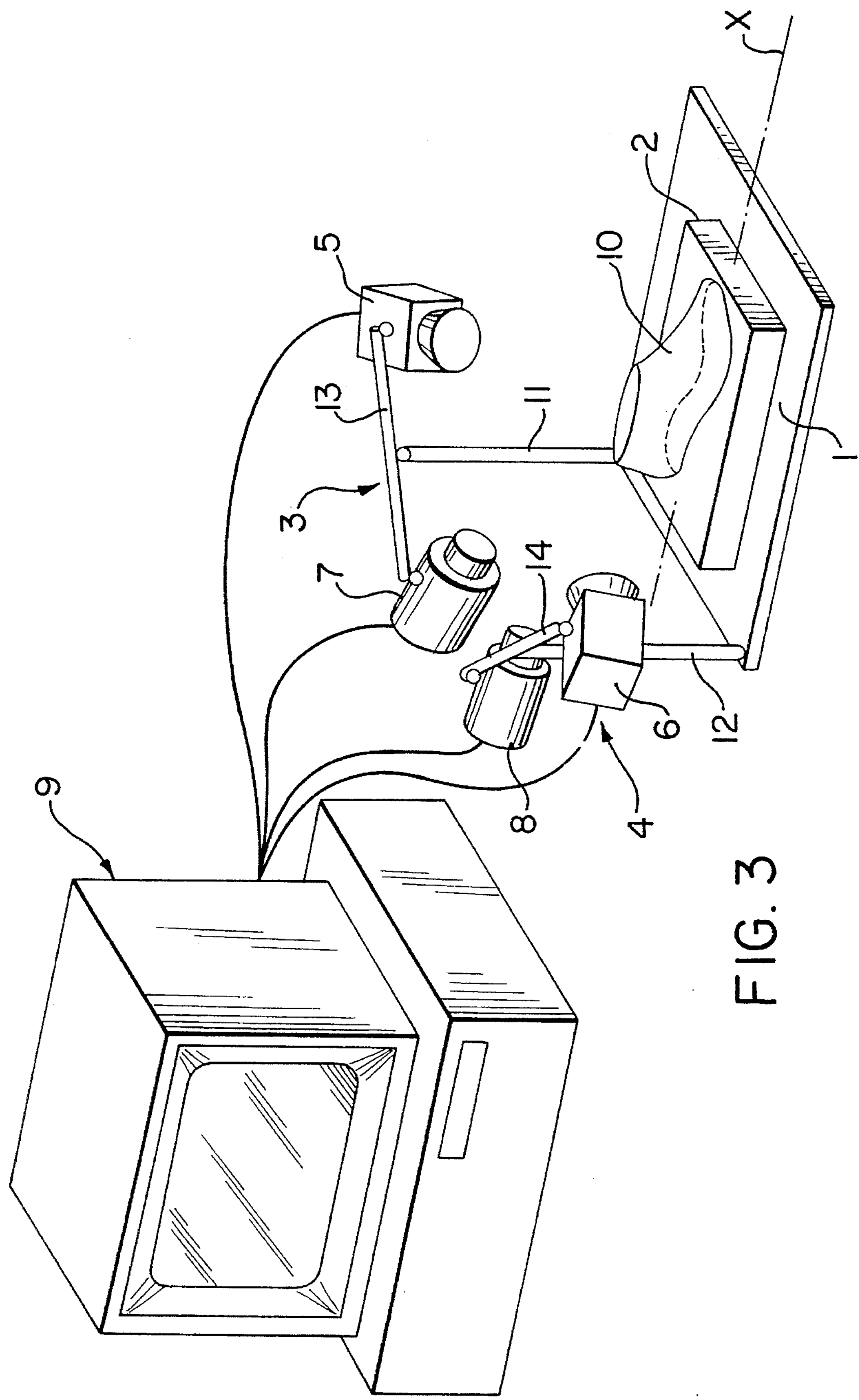
FIGS. 3 and 4 relate respectively to FIGS. 1 and 2 but, in this case, the sensors are located off-centre on either side of the cradle axis.

FIG. 3 shows, in the same way as FIG. 1, a measurement of the upper side of the foot; however, in this FIG. 3, the sensors are positioned laterally, that is to say either side of the axis, e.g. symmetrical with respect to the X axis. In this instance, arm 13 is horizontal and, clearly can be positioned as required. The heel of the foot points to sensors 3,4 in such a way that camera 5 can takes a posterior, superior and medial shot (inside of the right foot in the case of the figure), and camera 6 takes a posterior, superior and lateral shot (outside of the right foot).

Figure 4:
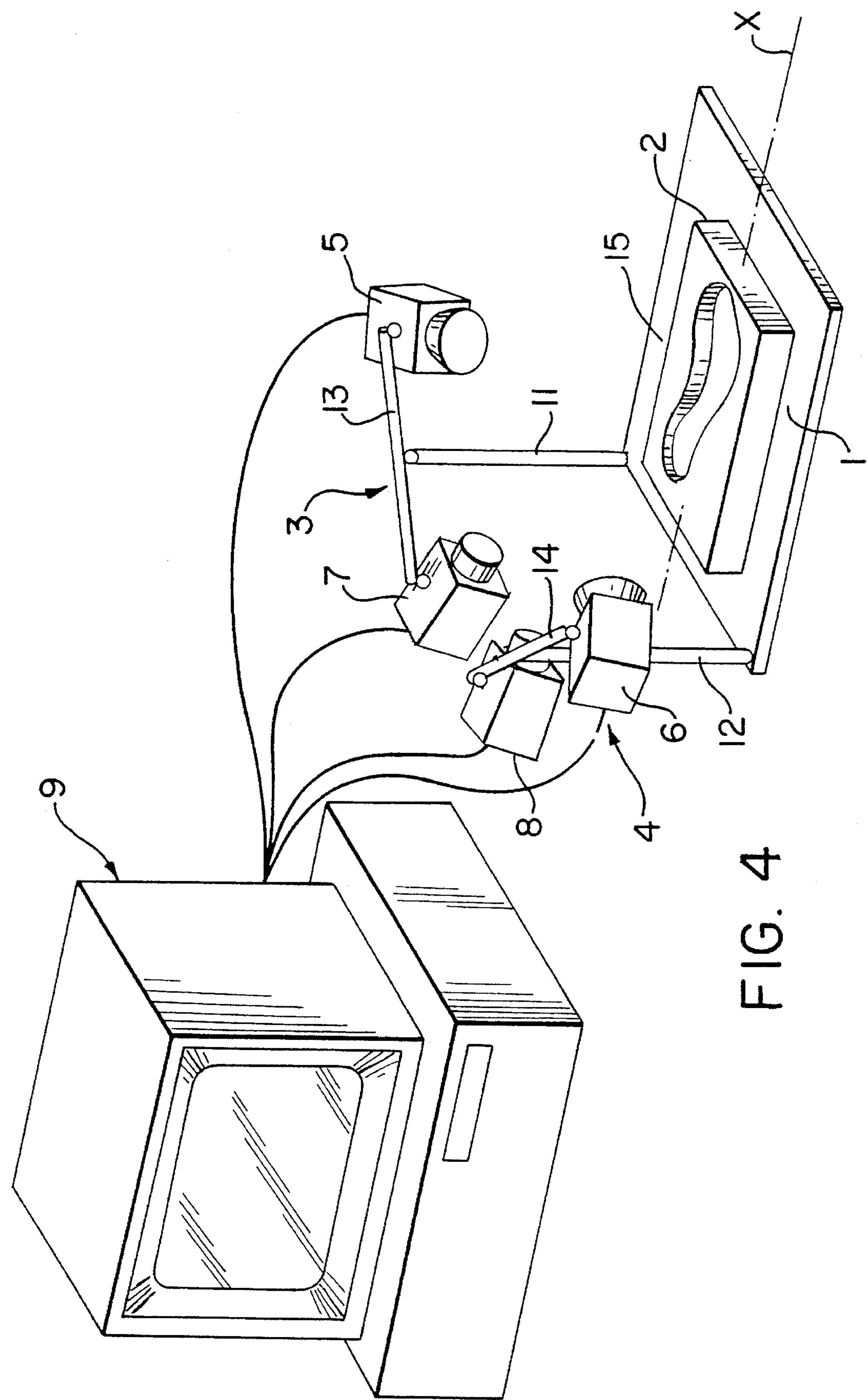

FIG. 4 is identical to FIG. 3 as far as sensor position is concerned. The foot has been removed from the flexible cradle 12, leaving imprint 15 and both cameras record the latter.

Whether the overall measurement of the foot is effected per FIGS. 1 and 2 or per FIGS. 3 and 4, the computer regroups all measurements in order to establish the overall form of the foot using a multiplicity of points which are each determined by three coordinates. All these points are recorded on a medium which can be magnetic and which will be used to calculate the appropriate last and its production. Three-dimensional data for this last can be used to calculate the patterns, that is to say to cut out the leather components required to make the shoes.

Clearly, the equipment can be fitted with a third sensor (e.g. sensor 4 in FIG. 1 added to both sensors seen in FIG. 3, and even a fourth sensor, thereby enhancing measurement accuracy or enabling more complex shapes to be measured, such as those associated specifically with certain cases of foot pathology.

In the case of FIG. 3, the equipment may also incorporate two sensors which can each be moved along an axis which is parallel to the X axis when using sensors which have to be moved, or even a single sensor mounted on a single post, moving sideways for both the inner and outer surfaces of the foot.

Any non-contact type sensor may be used.

I claim:

1. Tridimensional measurement process which involves no contact with the outer surface of an object and measures by digitization using a sensor linked to a computer and is distinguished by the locating of the object on a flexible cradle, the process comprising a two phase measurement of the object, the first phase including the steps of measuring the upper part of the object and removing the object from the cradle, the second phase including the step of measuring the imprint left by the object, and processing the measurements thereby providing an overall reconstruction of the object.

2. Process according to claim 1, distinguished by the fact that it consists in at least two pictures being taken during the first measurement phase, and at least one during the second measurement phase.

3. Process according to claim 2, distinguished by the fact it consists in one first phase picture being a posterior, superior and axial shot, and the other anterior superior and axial.

4. Process according to claim 2, distinguished by the fact that one of the two first phase measurement pictures is posterior, superior and lateral and the other posterior, superior and medial.

5. Process according to claim 4, distinguished by the fact that it comprises a third picture which is anterior, superior and axial.

6. Measurement process according to claim 2, distinguished by the fact that the second phase picture is a superior, axial shot which can be either anterior or posterior.

7. Measurement process according to claim 2, distinguished by the fact that the second measurement phase comprises two superior, axial shots, one of which is anterior and the other posterior.

8. Measurement process according to claim 2, distinguished by the fact that the second measurement phase requires two pictures, one posterior, superior and lateral shot and one posterior, superior and medial shot.

9. Tridimensional contact-free equipment for measuring the outer form of an object using digitization, via at least one sensor (3,4), linked to a computer (9), distinguished by its flexible cradle (2) supporting the object to be measured (10).

10. Equipment according to claim 9, distinguished by the sensor which consists of a projector (7,8) and a camera (5,6) which, between them, form a predetermined angle, the projector and the camera being separated by a specific distance.

11. Equipment according to claim 10 distinguished by its mobile sensor capable of taking shots from at least two viewing angles.

12. Equipment according to claim 10 distinguished by having several sensors which are fixed in space.

13. Equipment according to claim 12 distinguished by having two sensors located along the support axis, one taking posterior, superior shots, the other taking anterior, superior shots.

14. Equipment according to claim 12, distinguished by having two sensors offset from the cradle's axis, one taking posterior, superior and lateral shots, the other taking posterior, superior and medial shots.

* * * * *